US012807559B2

(12) United States Patent
Kim et al.

(10) Patent No.: US 12,807,559 B2
(45) Date of Patent: Nov. 24, 2026

(54) METHOD FOR PREPARING CARBONATE

(71) Applicant: LOTTE CHEMICAL CORPORATION, Seoul (KR)

(72) Inventors: Jin Hyung Kim, Daejeon (KR); Mi Hwa Baek, Daejeon (KR); Wang Gyu Kim, Daejeon (KR); Hyo Jin Jeon, Daejeon (KR); Eunhye Han, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 384 days.

(21) Appl. No.: 18/712,875

(22) PCT Filed: Nov. 23, 2022

(86) PCT No.: PCT/KR2022/018579
§ 371 (c)(1),
(2) Date: May 23, 2024

(87) PCT Pub. No.: WO2023/101296
PCT Pub. Date: Jun. 8, 2023

(65) Prior Publication Data

US 2025/0034076 A1 Jan. 30, 2025

(30) Foreign Application Priority Data

Nov. 30, 2021 (KR) ........................ 10-2021-0167926

(51) Int. Cl.
*C07C 68/06* (2020.01)

(52) U.S. Cl.
CPC .................................... *C07C 68/06* (2013.01)

(58) Field of Classification Search
None
See application file for complete search history.

(56) References Cited

U.S. PATENT DOCUMENTS

2024/0199527 A1 * 6/2024 Enomoto ................ C07C 68/08

FOREIGN PATENT DOCUMENTS

| | | | |
|---|---|---|---|
| CN | 103804124 | B | 7/2015 |
| CN | 113582845 | A | 11/2021 |
| CN | 113636935 | A | 11/2021 |
| JP | 2010168365 | A | 8/2010 |
| JP | 2011511791 | A | 4/2011 |
| JP | 2012092096 | A | 5/2012 |
| JP | 2015515450 | A | 5/2015 |

(Continued)

OTHER PUBLICATIONS

International Search Report issued in corresponding International Application No. PCT/KR2022/018579 mailed Mar. 17, 2023 (5 pages).

(Continued)

*Primary Examiner* — George W Kosturko
*Assistant Examiner* — Jason M. Nolan
(74) *Attorney, Agent, or Firm* — Osha Bergman Watanabe & Burton LLP

(57) ABSTRACT

The present invention relates to a method for preparing a carbonate. The method for preparing a carbonate of the present invention can effectively prepare high-purity EMC and DEC with a high DMC conversion rate. The method of the present invention can reduce energy costs and maintenance costs by reducing a load on a heat exchanger.

7 Claims, 1 Drawing Sheet

(56) References Cited

FOREIGN PATENT DOCUMENTS

| | | | | |
|---|---|---|---|---|
| JP | 2020152722 A | | 9/2020 | |
| JP | 2020527150 A | | 9/2020 | |
| KR | 10-2011-0105379 A | | 9/2011 | |
| WO | WO-2022230776 A1 | * | 11/2022 | ............. C07C 68/08 |

OTHER PUBLICATIONS

Written Opinion issued in corresponding International Application No. PCT/KR2022/018579 mailed Mar. 17, 2023 (4 pages).

* cited by examiner

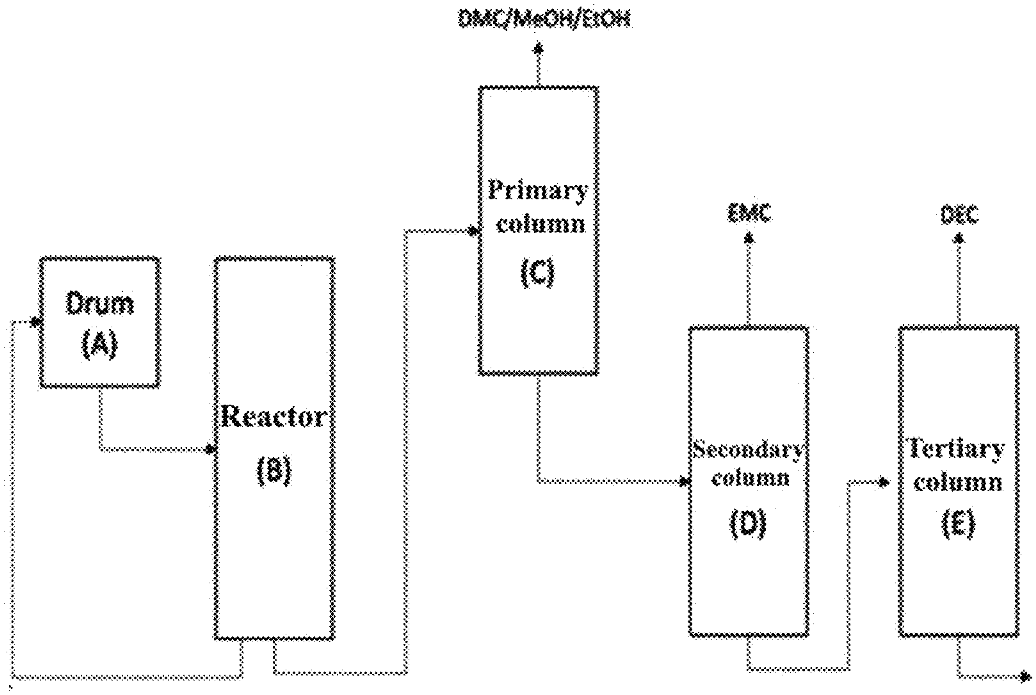
DMC/MeOH/EtOH
Primary column
(C)
EMC
DEC
Drum
(A)
Reactor
(B)
Secondary column
(D)
Tertiary column
(E)

METHOD FOR PREPARING CARBONATE

TECHNICAL FIELD

The present invention relates to a method for preparing a carbonate. Particularly, the present invention relates to a method capable of purifying a target product with high purity from a product of a carbonate preparation reaction.

BACKGROUND ART

As an organic solvent for a battery electrolyte, ethyl methyl carbonate (EMC) and diethyl carbonate (DEC) are mainly used. The EMC and DEC are prepared by transesterification of dimethyl carbonate (DMC) and ethanol (EtOH). The transesterification is also a reversible reaction. In addition, the transesterification may also be performed in the presence of a catalyst. Reaction Formula 1 below shows the transesterification (in which, MeOH is an abbreviation for methanol):

[Reaction Formula 1]

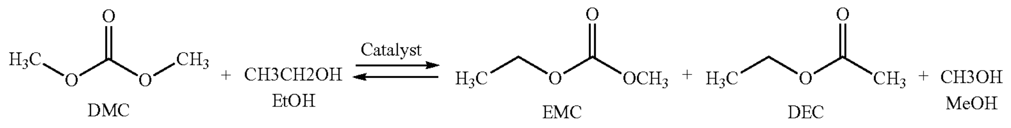

DMC
CH3CH2OH
EtOH
EMC
DEC
CH3OH
MeOH

A catalyst applied to the reaction includes basic catalysts (NaOH, KOH, etc.) with excellent activity. However, the basic catalysts have low solubility in organic solvents, especially carbonates, and thus are not dissolved in DMC, EMC and DEC. Therefore, the basic catalysts cause column plugging, which is the cause of process defects in a reactive distillation process or purification process. That is, usually, the catalyst applied to the reaction is removed and then post-processing (e.g., separation and purification, etc.) is performed to produce a carbonate. The problem mainly occurs in a fluidized bed reactor.

Patent Document 1 discloses a method for preparing a carbonate using DMC, alcohol, and a sodium methoxide catalyst. In Patent Document 1, EMC and DEC are prepared through reactive distillation. Here, Patent Document 1 is intended to efficiently remove the catalyst by installing a strainer for separating solids (catalysts) at the rear end of a distillation column where reactive distillation is performed. However, when alcohol is distilled in the reactive distillation column, the catalyst is precipitated in the process. Accordingly, plugging occurs in the column because the precipitated catalyst accumulates inside the distillation column. In addition, Patent Document 1 uses two additional reactive distillation columns (second and third reaction distillation columns) except for a distillation column (first reactive distillation column) used for reaction distillation in a process of recovering the products EMC and DEC. Here, DEC is obtained from the bottom of the second reactive distillation column, and EMC is obtained from the bottom of the third reactive distillation column. When the product is obtained from the bottom of the distillation column, the product contains metals and impurities generated during the process, thereby making it difficult to obtain a high-purity carbonate. When the carbonate is applied to lithium-ion batteries, the battery resistance increases. In addition, in order to first obtain DEC (boiling point: 125.8 °C), which has a higher boiling point than EMC (boiling point: 107 °C), a higher heat (transfer) load and heat transfer rate are required in a heat exchanger after the reaction. Therefore, according to the method of Patent Document 1, energy costs increase.

Patent Document 2 discloses a method for preparing a carbonate through extractive distillation by using a gel-type strong basic ion exchange resin catalyst as a transesterification catalyst. The extractive distillation requires a separation process of separating the product with an extractant, which increases equipment and energy costs. In addition, since an ion exchange resin catalyst usually has a low strength, the deactivation progresses quickly due to a loss of exchange groups and formation of fine powder. As a result, since the pressure in the reactor also increases, the catalyst needs to be replaced periodically. In addition, since a trace of extractant may be present in the carbonate, additional processes are required to increase the purity.

Therefore, research is required on methods capable of effectively preparing high-purity EMC and DEC with a high DMC conversion rate.

PRIOR ARTS

Patent Documents (Patent Document 1) CN 103804124 B
(Patent Document 2) KR 10-2011-0105379 A

DISCLOSURE

Technical Problem

An object of the present invention is to effectively prepare high-purity EMC and DEC with a high DMC conversion rate.

Another object of the present invention is to reduce energy costs and maintenance costs by reducing a load on a heat exchanger.

Technical Solution

An aspect of the present invention provides a method for preparing a carbonate including a first step of preparing a product containing ethyl methyl carbonate, diethyl carbonate, and methanol by adding raw materials containing dimethyl carbonate and ethanol into a fixed bed reactor system and inducing transesterification of the raw materials; a second step of separating a reactor effluent containing the product and the unreacted raw materials from a first separation system to obtain a first separation system overhead stream including ethanol, methanol and dimethyl carbonate as main components and a first separation system bottom stream including diethyl carbonate and ethyl methyl carbonate as main components; a third step of separating the first separation system bottom stream from a second separation system to obtain a second separation system overhead stream including ethyl methyl carbonate as a main component, and a second separation system bottom stream including diethyl carbonate as a main component; and a fourth step of separating the second separation system bottom stream from a third separation system to obtain a third separation system overhead stream including diethyl carbonate as a main component, in which any one of the second to fourth steps sets a reflux ratio of any one of the first to third separation systems in the range of 0.5 to 5.

Advantageous Effects

According to the method for preparing the carbonate of the present invention, it is possible to effectively prepare high-purity EMC and DEC with a high DMC conversion rate.

Further, it is possible to reduce energy costs and maintenance costs by reducing a load on a heat exchanger.

DESCRIPTION OF DRAWINGS

FIG. 1 is a schematic diagram of a method for preparing a carbonate according to the present invention.

BEST MODE OF THE INVENTION

Hereinafter, the contents of the present invention will be described in more detail.

The present invention relates to a method for preparing a carbonate. Specifically, the present invention relates to a method for preparing a liquid carbonate or a carbonate-based solvent. The present invention is intended to obtain a carbonate with high purity. In addition, the present invention is intended to easily perform a process of obtaining the carbonate with high energy efficiency and low costs.

The present invention is intended to prepare a carbonate obtained by transesterification of DMC and ethanol. To this end, in the present invention, largely, transesterification of DMC and ethanol is performed, and then a process of purifying the reaction product is performed.

To this end, the method of the present invention proceeds through at least four steps.

In the method of the present invention, in a first step, a product containing ethyl methyl carbonate, diethyl carbonate, and methanol is prepared by adding raw materials containing dimethyl carbonate and ethanol into a fixed bed reactor system, and inducing transesterification of the raw materials.

The product containing ethyl methyl carbonate, diethyl carbonate, and methanol may be prepared through transesterification of dimethyl carbonate and ethanol.

The reactors using the catalyst are broadly divided into two types. The first type is a fluidized bed reactor, and the second type is a fixed bed reactor.

In the fluidized bed reactor, literally, the catalyst flows in the reactor. For this reason, since the catalyst may be included in the product, it is required to remove the catalyst before the process of separating or purifying the product. This is because when the catalyst is not removed, column plugging occurs, which is the cause of defects in the separation and/or purification process.

In the fixed bed reactor, the catalyst is present in the fixed state in the reactor. Accordingly, even when the reaction is completed, the catalyst is still present in the reactor, so that the product does not contain the catalyst. Therefore, when using the fixed bed reactor, a separate process of removing the catalyst is not required. In the present invention, the fixed bed reactor is applied. As a result, the method of the present invention does not require a process of removing the catalyst applied to the reaction, and there is no risk of the above-mentioned problems occurring due to the catalyst.

In the present invention, the raw materials prepared above are added into the reactor system. In this specification, the term "reactor system" is used as a concept of encompassing other facilities attached to the reactor, or other additional reactors, not the reactor alone. That is, the reactor system includes a single reactor and other facilities attached thereto, a plurality of reactors, or a plurality of reactors and other facilities attached thereto.

In the method of the present invention, the transesterification of dimethyl carbonate and ethanol in the raw materials is performed in the reactor system. As a result, the product including ethyl methyl carbonate (EMC), diethyl carbonate (DEC), and methanol (MeOH) is prepared. This product is discharged from the reactor system as a reactor effluent, together with unreacted raw materials. As described above, since the method of the present invention uses the fixed bed reactor, the reactor effluent may not contain catalyst.

In the method of the present invention, in a second step, the reactor effluent containing the product and the unreacted raw materials is separated. Specifically, in the method of the present invention, the reactor effluent containing the product and the unreacted raw materials is separated from a first separation system to obtain a first separation system overhead stream including ethanol, methanol and dimethyl carbonate as main components and a first separation system bottom stream including diethyl carbonate and ethyl methyl carbonate as main components. More specifically, in the method of the present invention, in the second step, the reactor effluent is supplied to the first separation system, and the first separation system discharges low boiling-point components of the reactor effluent from the column overhead of the first separation system, and discharges high boiling-point components of the reactor effluent from the column bottom of the first separation system.

In this specification, a stream discharged from the column overhead of the separation system is referred to as a separation system overhead stream.

In this specification, a stream discharged from the column bottom of the separation system is referred to as a separation system bottom stream.

Among the components included in the reactor effluent, the low-boiling point components include ethanol, methanol, and dimethyl carbonate as main components. In addition, among the components included in the reactor effluent, the high-boiling point components include diethyl carbonate and ethyl methyl carbonate as main components.

In this specification, the including of a specific component as a main component may mean that the corresponding component is included in a ratio of 60 wt % or more, 65 wt % or more, 70 wt % or more, 75 wt % or more, 80 wt % or more, 85 wt % or more, 90 wt % or more, 95 wt % or more, 97 wt % or more, or 99 wt % or more based on the total amount, and included in a ratio of less than 100 wt %, or approximately 100 wt %.

In addition, in this specification, the separation system is used as a concept of encompassing not only a separation column, which is a column-shaped structure that performs a separation process, but also a reboiler for reheating a part of the stream refluxed to the separation column in the bottom stream thereof, and a cooler for cooling a part of the stream refluxed to the separation column (or a condenser for condensing the stream thereof) in the overhead stream thereof.

In the method of the present invention, in a third step, the first separation system bottom stream is separated. Specifically, in the method of the present invention, in the third step, the first separation system bottom stream is separated from a second separation system to obtain a second separation system overhead stream including ethyl methyl carbonate as a main component and a second separation system bottom stream including diethyl carbonate as a main component. More specifically, in the method of the present invention, in the second step, the first separation system bottom stream is supplied to the second separation system and the first separation system bottom stream is separated from the second separation system to obtain a second separation system overhead stream including ethyl methyl carbonate as a main component and a second separation system bottom stream including diethyl carbonate as a main component.

In the method of the present invention, in a fourth step, the second separation system bottom stream is separated. Specifically, in the method of the present invention, in the fourth step, the second separation system bottom stream is separated from a third separation system to obtain a third separation system overhead stream containing diethyl carbonate as a main component. More specifically, in the method of the present invention, in the fourth step, the second separation system bottom stream is separated from a third separation system to obtain a third separation system overhead stream containing diethyl carbonate, which is a low boiling-point component as a main component and a third separation system bottom stream containing a residual heavier, which is a high boiling-point component as a main component. That is, in the present invention, in the fourth step, the second separation system bottom stream is supplied to the third separation system, and the second separation system bottom stream is separated from the third separation system to obtain a third separation system overhead stream containing diethyl carbonate as a main component.

The second to fourth steps are different from existing methods in which high boiling point components are first separated and discharged. In the steps, the low boiling point components are first separated and discharged. Through this, in the method of the present invention, it is possible to reduce a load on a heat exchanger required for separation, thereby reducing energy costs and maintenance costs.

In addition, in the present invention, a high-purity carbonate of 99.9% or more may be obtained only when the operating conditions of the separation system are appropriately adjusted. Specifically, in the method of the present invention, any one of the second to fourth steps sets a reflux ratio of any one of the first to third separation systems in the range of 0.5 to 5. That is, the reflux ratio of at least one of the separation systems applied in the present invention needs to be adjusted as above. In another embodiment, in at least two of the second to fourth steps, the reflux ratios of at least two of the first to third separation systems may be set in the range of 0.5 to 5.

Even if the same method as the present invention is applied, various problems occur when the reflux ratio of the entire separation system is out of the above range. Specifically, when the reflux ratio of the entire separation system is less than 0.5, a ratio of the amount of reflux liquid to the amount of effluent liquid at the column overhead is small, and thus the discharge amount of the product increases, but it is difficult to obtain a high-purity carbonate. In addition, if the reflux ratio of the entire separation system is more than 5, the ratio of the amount of reflux liquid to the amount of effluent liquid at the column overhead increases to obtain a high-purity carbonate. However, since the amount of effluent liquid is small, the product obtainment time increases and the operating cost increases.

In this specification, a reflux ratio (R) refers to a ratio of the amount of reflux liquid to the amount of effluent liquid. That is, based on the amount of liquid phase discharged from a specific column or reactor, the amount of liquid phase returning to the column or reactor may be referred to as the reflux ratio.

FIG. 1 briefly illustrates a process of performing the method of the present invention. The contents of FIG. 1 may be summarized as follows. A drum A is a container that stores a solution (sulfuric acid/NaOH, etc.) for reusing an ion exchange resin. The drum A may regenerate the ion exchange resin by circulating the solution when the efficiency of the ion exchange resin decreases. A reactor B is a reactor system. The reactor B operates with a plurality of fixed bed reactors connected in series. A bottom material discharged from the reactor is transmitted to a first separation system C. DMC/MeOH/EtOH is obtained at the top of the first separation system C and EMC/DEC is obtained at the bottom thereof. EMC is recovered from the top of a second separation system D. A bottom effluent is transmitted to a third separation system E. DEC is recovered from the top of the third separation system E, and a heavier is discarded from the bottom of the third separation system.

In an embodiment, a mixing ratio of reactants DMC and EtOH in the raw materials may also be appropriately adjusted. For example, a ratio (EtOH/DMC) of the weight of dimethyl carbonate (DMC) and the weight of ethanol (EtOH) in the raw materials may be in the range of 0.1 to 10. In another embodiment, the ratio (EtOH/DMC) may be 0.15 or higher or 0.2 or higher, and may be 9 or less, 8 or less, 7 or less, 6 or less, or 5 or less. Within the range, the reactants may properly contact the catalyst to perform the reaction, and waste of energy may be reduced in a subsequent purification process. In addition, the ratio between the reactants may also be adjusted depending on what a target product is. For example, since the demand for DEC is high, it is common to set the composition to increase its selectivity by using DEC as a target product, but it is expected that the demand for EMC is high in the future.

The reactor system may also be designed appropriately.

In an embodiment, the fixed bed reactor may be a fixed bed reactor filled with an ion exchange resin catalyst. It is possible to maximize a contact with reactants by applying the appropriate ion exchange resin catalyst. As a result, it is possible to prepare the target product, carbonate with a fast reaction rate and high reaction efficiency. In an embodiment, the ion exchange resin catalyst may be a basic ion exchange resin catalyst or an acidic ion exchange resin catalyst. Specifically, the ion exchange resin catalyst may be a basic ion exchange resin catalyst.

The acidic ion exchange resin may be divided into a strongly acidic ion exchange resin and a weakly acidic ion exchange resin. Usually, the strongly acidic ion exchange resin catalyst may be used, and in this case, the resin catalyst may have a sulfonate ion as an exchange group and a hydrogen ion as an ion type.

The basic ion exchange resin catalyst may be divided into a weakly basic ion exchange resin catalyst and a strongly basic ion exchange resin catalyst. The strongly basic ion exchange resin catalyst may have bromide anion ($Br^-$), thiocyanate ($SCN^-$) anion, chlorine anion ($Cl^-$), acetate anion (acetate, $CH_3COO^-$), hydroxyl anion ($OH^-$), fluorine anion ($F^-$), etc. as ionic types. The weakly basic ion exchange resin catalyst may have citrate anion ($C_3H_5O(COO)_3^{3-}$), sulfate ($SO_4^{2-}$), etc. as ionic types.

In an embodiment, the ion exchange resin catalyst may be a porous ion exchange resin catalyst or a gel-type ion exchange resin catalyst. Specifically, the ion exchange resin catalyst may be a porous ion exchange resin catalyst. A porous ion exchange resin has many (about 10 to 1,000) macropores on the surface to be chemically more stable than a gel-type resin. In addition, the porous ion exchange resin may have a large surface area to maximize a contact area with reactants.

The porous ion exchange resin may have excellent decolorization to relatively reduce the washing time of the ion exchange resin and the amount of washing solvent used at the early reaction. In addition, the porous ion exchange resin has high strength, and when reused, a loss of the exchange groups and formation of fine powder are small, so that the reuse cycle is long.

In an embodiment, the ion exchange resin catalyst may have an exchange capacity of 1 (eq/l-wet resin) or more and 1.5 (eq/l-wet resin) or less. In general, as the crosslinking degree of the ion exchange resin increases, the exchange capacity tends to be large because more exchange groups are attached to the parent matrix. However, when the crosslinking degree of the ion exchange resin is high, the number of exchange groups participating in the reaction decreases due to the strong bond between the parent matrix and the exchange groups, and thus the reaction efficiency decreases. Accordingly, the strength may be maintained even under an appropriate reaction rate and a rapid volume change within the exchange capacity range.

Therefore, it may be most advantageous to apply an ion exchange resin catalyst that satisfies all of the characteristics. In an embodiment, the fixed bed reactor system includes a fixed bed reactor filled with a basic ion exchange resin catalyst, the basic ion exchange resin is porous, and the exchange capacity of the basic ion exchange resin may be in the range of 1 (eq/l-wet resin) to 1.5 (eq/l-wet resin).

In addition, the present invention may appropriately design reactor facilities of the reactor system. In the present invention, the fixed bed reactor system may be a system having a plurality of fixed bed reactors. That is, the fixed bed reactor system may include two or more fixed bed reactors. In addition, in the present invention, the fixed bed reactor system may connect the plurality of fixed bed reactors in series. Here, the connecting of the plurality of reactors in series means that an outlet of one reactor is connected to an inlet of the other reactor. In an embodiment, the fixed bed reactor system may include a plurality of fixed bed reactors connected in series.

In the reactor system, the number of fixed bed reactors may be appropriately adjusted. The fixed bed reactor system may be a system in which 2 to 10 fixed bed reactors are connected in series.

Unlike existing methods, in the present invention, reactive distillation or extractive distillation may not be performed. That is, the method of the present invention may be applied with a tray column or packing column as the separation system. Since the meaning of the tray column and the packing column is known, the detailed descriptions will be omitted. Since theoretical and empirical data related to the design are rich, it possible to design a systematic separation and purification system by using the tray column and the packing column. That is, in an embodiment, the first to third separation systems may all be tray columns or packing columns.

When the previous process has corresponded to the reaction process in the method of the present invention, a process to be described below may be a separation (or purification) process. The operating conditions of the separation system applied during the separation or purification process using the separation system may also be appropriately adjusted.

The separation and purification conditions in the second step may also be appropriately adjusted.

In one example, the fourth step may be applied with a separation system with the theoretical number of stages in the range of 15 to 80 stages as the first separation system. Within the above range, a separation system may be manufactured economically at the same time while exhibiting appropriate stage efficiency. In addition, within the range, maintenance is easy and the heat balance of the separation system may be easily adjusted.

In one example, in the second step, the reflux ratio of the first separation system may be set in the range of 0.5 to 5. The effect of this setting is the same as described above.

In addition, the combination of the first and second steps has a mechanism similar to that of conventional reactive distillation. However, in the third and fourth steps, the target products are discharged in the order of boiling points through the column overhead, which is a clear difference from the conventional method of discharging the target products in the opposite order through the column bottom. In particular, in the present invention, to this end, it is required to adjust the operating conditions in each of the second to fourth steps.

In one example, in the second step, the temperature of the reboiler of the first separation system may be set in the range of 90 °C to 100 °C. At this time, the overhead stream of the first separation system may contain ethanol, methanol, and DMC as main components, and the bottom stream of the first separation system may contain DEC and EMC as main components.

The separation and purification conditions in the third step may also be appropriately adjusted.

In one example, the third step may be applied with a separation system with the theoretical number of stages in the range of 15 to 80 stages as the second separation system. Within the above range, the separation system may be manufactured economically at the same time while exhibiting appropriate stage efficiency. In addition, within the range, maintenance is easy and the heat balance of the separation system may be easily adjusted.

In one example, in the third step, the reflux ratio of the second separation system may be set in the range of 0.5 to 5. The effect of this setting is the same as described above.

In one example, in the third step, the temperature of the reboiler of the second separation system may be set in the range of 110 °C to 120 °C. At this time, the overhead stream of the second separation system may contain EMC as a main component, and the bottom stream of the second separation system may contain DEC as a main component.

The separation and purification conditions in the fourth step may also be appropriately adjusted.

In one example, the fourth step may be applied with a separation system with the theoretical number of stages in the range of 15 to 80 stages as the third separation system. Within the above range, the separation system may be manufactured economically at the same time while exhibiting appropriate stage efficiency. In addition, within the range, maintenance is easy and the heat balance of the separation system may be easily adjusted.

In one example, in the fourth step, the reflux ratio of the third separation system may be set in the range of 0.5 to 5. The effect of this setting is the same as described above.

In one example, in the fourth step, the temperature of the reboiler of the third separation system may be set in the range of 130 °C. to 140 °C. At this time, the overhead stream of the third separation system may contain DEC as a main component, and the bottom stream of the third separation system may contain a residual heavier as a main component.

Meanwhile, the method for preparing the carbonate of the present invention may further include conventional steps known in the art before or after each of the steps, in addition to the above-described steps.

Hereinafter, the present invention will be described in more detail. However, the following Examples do not limit the content of the present invention.

[Gas Chromatography]

The analysis of the purity of a product and the contents of impurities and heavier in the product were conducted using gas chromatography (GC). Specifically, GC was performed on a sample in which 1 g of an analyte material was taken and mixed with 0.1 g of m-xylene. An YL6500GC product from YOUNGIN Chromas was used as the GC equipment, in which a GC column was DB-1 30 m*0.32 mm from Agilent and a GC detector was FID.

[ICP-AES]

The analysis of the metal content in the product was measured using inductively coupled plasma atomic emission spectroscopy (ICP-AES). An Optima 8300 model from Perkin Elmer was used. 10 g of an effluent sample was mixed with 10 ml of 70% nitric acid and 10 ml of water, heated at 250 °C. for 2 hours, and then analyzed.

[Color]

Product colors were evaluated by APHA. The APHA is also called Hazen or Pt/Co color, which refers to the yellowness of a liquid sample. For APHA measurement, an automatic color meter from Tintometer, a PFX 995 model, was used. A sample was filled with about ¾ of a cell height, disposed in close contact with a right position, and then analyzed by setting a temperature to room temperature and pressing a READ key. After measuring three times, an average value was taken as a result value.

EXAMPLES

A reaction system was prepared in which four fixed bed reactors were connected in series. An ion exchange resin for each reactor was filled with 80 cc (58 g) of a highly basic porous anion exchange resin (Samyang Corporation, Trilte AMP-18), which had trimethylammonium (TMA) ions as an exchange group, chlorine ions as an ion type, and an exchange capacity of 1.3 eq/L. The raw materials included ethanol (EtOH) and DMC at a mass ratio (EtOH/DMC) of 0.8. The system was operated while continuously supplying raw materials to the reactor system at 2 cc/min and maintaining the temperature of the system at 70 °C.

The reaction product was supplied to a first separation system. The number of stages of the first separation system was 60. Separation was performed at a reflux ratio of 3, normal pressure, and a reboiler temperature of 93 to 100 °C. An effluent containing DMC, EtOH, and MeOH as main components was obtained from the column overhead, and an effluent containing EMC and DEC as main components was obtained from the column bottom.

The bottom effluent from the first separation system was supplied to a second separation system. The number of stages of the second separation system was 60. Separation was performed at a reflux ratio of 3, normal pressure, and a reboiler temperature of 110 to 120 °C. From the column overhead of the second separation system, EMC with the purity of 99.9% or more and a total metal content of 1 ppm or less was obtained. An effluent containing DEC as a main component was obtained from the column bottom of the second separation system.

The bottom effluent of the second separation system was supplied to a third separation system. The number of stages of the third separation system was 60. Separation was performed at a reflux ratio of 3, normal pressure, and a reboiler temperature of 130 to 140 °C. From the column overhead of the third separation system, DEC with the purity of 99.9% or more and a total metal content of 1 ppm or less was obtained. The heavier obtained from the column bottom of the third separation system was discarded.

Comparative Example 1

The same process as Example 1 was performed, except that the reflux ratios in the first to third separation systems were all set to 0.3.

Comparative Example 2

The same process as Example 1 was performed, except that the third separation system was not applied and the operation was performed to obtain the bottom stream of the second separation system containing DEC as the main component. The results of Examples and Comparative Examples 1 and 2 were compared and shown in Tables 1 and 2 below.

TABLE 1

| | Purity | EMC [%] | DEC [%] |
|---|---|---|---|
| Result | Example | 99.99 | 99.99 |
| | Comparative Example 1 | 99.8 | 99.8 |

TABLE 2

| | Classification | Example | Comparative Example 2 |
|---|---|---|---|
| Result | DEC purity [%] | 99.99 | 99.5 |
| | Impurity/Heavier content [%] | — | 0.5 |
| | DEC total metal content [ppm] | 1 | 5 |
| | APHA (color) | 3 | 10 |

According to Table 1, it may be confirmed that it is required to satisfy the reflux ratio of the separation system according to the present invention. If the reflux ratio is less than 0.5, a ratio of the amount of reflux liquid to the amount of effluent liquid in the column overhead is small, and the discharge amount of the product increases. However, it is difficult to obtain a carbonate with high purity of 99.9% or higher.

According to Table 2, if the number of separation systems is not sufficiently used and DEC is obtained at the column bottom, it is difficult to obtain a high-purity carbonate. In this case, since there are many impurities and the APHA value is too high, it is difficult to use the carbonate as an organic solvent for lithium ion batteries. Therefore, considering the high purity, the metal content, and the APHA value, it may be seen that the carbonate should be prepared in the same manner as the method of the present invention.

The invention claimed is:

1. A method for preparing a carbonate comprising:

a first step of preparing a product containing ethyl methyl carbonate, diethyl carbonate, and methanol by adding raw materials containing dimethyl carbonate and ethanol into a fixed bed reactor system and inducing transesterification of the raw materials;

a second step of separating a reactor effluent containing the product and the unreacted raw materials from a first separation system to obtain a first separation system overhead stream including ethanol, methanol and dimethyl carbonate as main components and a first separation system bottom stream including diethyl carbonate and ethyl methyl carbonate as main components;

a third step of separating the first separation system bottom stream from a second separation system to obtain a second separation system overhead stream including ethyl methyl carbonate as a main component, and a second separation system bottom stream including diethyl carbonate as a main component; and a fourth step of separating the second separation system bottom stream from a third separation system to obtain a third separation system overhead stream including diethyl carbonate as a main component, wherein any one of the second to fourth steps sets a reflux ratio of any one of the first to third separation systems in the range of 0.5 to 5.

2. The method for preparing the carbonate of claim 1, wherein the fixed bed reactor system includes a fixed bed reactor filled with a basic ion exchange resin catalyst, the basic ion exchange resin is porous, and the exchange capacity of the basic ion exchange resin is in the range of 1 (eq/l-wet resin) to 1.5 (eq/l-wet resin).

3. The method for preparing the carbonate of claim 1, wherein the fixed bed reactor system includes a plurality of fixed bed reactors connected in series.

4. The method for preparing the carbonate of claim 1, wherein the first separation system to the third separation system are tray columns or packing columns.

5. The method for preparing the carbonate of claim 1, wherein in the second step, a separation system with the theoretical number of stages in the range of 15 to 80 stages is applied as the first separation system, the reflux ratio of the first separation system is set in the range of 0.5 to 5, and the temperature of a reboiler of the first separation system is set in the range of 90 °C to 100 °C.

6. The method for preparing the carbonate of claim 1, wherein in the third step, a separation system with the theoretical number of stages in the range of 15 to 80 stages is applied as the second separation system, the reflux ratio of the second separation system is set in the range of 0.5 to 5, and the temperature of a reboiler of the second separation system is set in the range of 110 °C to 120 °C.

7. The method for preparing the carbonate of claim 1, wherein in the fourth step, a separation system with the theoretical number of stages in the range of 15 to 80 stages is applied as the third separation system, the reflux ratio of the third separation system is set in the range of 0.5 to 5, and the temperature of a reboiler of the third separation system is set in the range of 130 °C to 140 °C.

* * * * *